(12) United States Patent
Flock et al.

(10) Patent No.: US 7,889,340 B1
(45) Date of Patent: *Feb. 15, 2011

(54) NORMAL INCIDENCE ELLIPSOMETER WITH COMPLEMENTARY WAVEPLATE ROTATING COMPENSATORS

(75) Inventors: Klaus Flock, Mountain View, CA (US); Jeff T. Fanton, Los Altos, CA (US)

(73) Assignee: KLA-Tencor Corporation, San Jose, CA (US)

( * ) Notice: Subject to any disclaimer, the term of this patent is extended or adjusted under 35 U.S.C. 154(b) by 267 days.

This patent is subject to a terminal disclaimer.

(21) Appl. No.: 12/170,371

(22) Filed: Jul. 9, 2008

Related U.S. Application Data

(60) Provisional application No. 61/034,112, filed on Mar. 5, 2008, provisional application No. 61/034,049, filed on Mar. 5, 2008.

(51) Int. Cl.
*G01J 4/00* (2006.01)
(52) U.S. Cl. .................. 356/369; 356/364; 356/365; 356/366; 356/367; 356/368
(58) Field of Classification Search ......... 356/364–370, 356/72–73; 250/225
See application file for complete search history.

(56) References Cited

U.S. PATENT DOCUMENTS

| | | | |
|---|---|---|---|
| 5,798,837 A | 8/1998 | Aspnes et al. | |
| 5,872,630 A * | 2/1999 | Johs et al. | 356/369 |
| 5,877,859 A * | 3/1999 | Aspnes et al. | 356/364 |
| 5,910,842 A | 6/1999 | Piwonka-Corle et al. | |
| 5,973,787 A | 10/1999 | Aspnes et al. | |
| 6,373,614 B1 * | 4/2002 | Miller | 359/237 |
| 6,417,892 B1 * | 7/2002 | Sharp et al. | 348/742 |
| 6,449,043 B2 | 9/2002 | Aspnes et al. | |
| 6,515,744 B2 * | 2/2003 | Wei | 356/369 |
| 6,822,738 B1 * | 11/2004 | Johs et al. | 356/369 |
| 6,882,421 B2 * | 4/2005 | Opsal et al. | 356/369 |
| 7,173,700 B2 | 2/2007 | Aspnes | |
| 7,349,079 B2 * | 3/2008 | Zhao et al. | 356/128 |
| 7,420,675 B2 * | 9/2008 | Giakos | 356/364 |
| 7,428,050 B2 * | 9/2008 | Giakos | 356/369 |
| 7,499,175 B1 * | 3/2009 | Palmer et al. | 356/450 |

(Continued)

OTHER PUBLICATIONS

Office Action dated Jun. 23, 2010 for U.S. Appl. No. 12/170,367.

(Continued)

*Primary Examiner*—Sang Nguyen
(74) *Attorney, Agent, or Firm*—Joshua D. Isenberg; JDI Patent (57) ABSTRACT

In embodiments of the present invention a second, different waveplate is introduced into a single rotating compensator normal incidence ellipsometer. The second waveplate provides a quarter wavelength retardation that is different from and complementary to that of the first waveplate in order to increase the spectral range for which useful retardation is available, especially towards the deep UV spectrum. The sensitivity for the system may also be increased in the conventional spectral range, since each of the two waveplates may be optimized for its own, somewhat more narrow spectral range of operation. With the proper choice of two waveplates of different retardation, the useful spectral range may be extended from typically 190-820 nm to 150-1000 nm, and beyond if necessary, while increasing the sensitivity within the conventional wavelength range at the same time.

29 Claims, 5 Drawing Sheets

U.S. PATENT DOCUMENTS 7,701,561 B2 * 4/2010 Zou et al. .................... 356/73

OTHER PUBLICATIONS

U.S. Appl. No. 61/034,112, entitled "Normal Incidence Ellipsometer With Complementary Waveplate Rotating Compensators", filed Mar. 5, 2008.

U.S. Appl. No. 61/034,049, entitled "Complementary Waveplate Dual Rotating Compensator Ellipsometer", filed Mar. 5, 2008.

U.S. Appl. No. 12/170,367, entitled "Complementary Waveplate Dual Rotating Compensator Ellipsometer" filed Jul. 9, 2008.

Notice of Allowance and Fees Due dated Oct. 1, 2010 for U.S. Appl. No. 12/170,367.

* cited by examiner

NORMAL INCIDENCE ELLIPSOMETER WITH COMPLEMENTARY WAVEPLATE ROTATING COMPENSATORS

CLAIM OF PRIORITY

This application claims the benefit of priority of commonly-assigned U.S. Patent Application No. 61/034,112, entitled "NORMAL INCIDENCE ELLIPSOMETER WITH COMPLEMENTARY WAVEPLATE ROTATING COMPENSATORS", filed Mar. 5, 2008, the entire contents of which are incorporated herein by reference.

This application claims the benefit of priority of commonly-assigned U.S. Patent Application No. 61/034,049, entitled "COMPLEMENTARY WAVEPLATE DUAL ROTATING COMPENSATOR ELLIPSOMETER", filed Mar. 5, 2008, the entire contents of which are incorporated herein by reference.

CROSS REFERENCE TO RELATED APPLICATION

This application is related to commonly-assigned co-pending U.S. patent application Ser. No. 12/170,367, entitled "COMPLEMENTARY WAVEPLATE ROTATING COMPENSATOR ELLIPSOMETER", which is filed the same date as the present application, the entire contents of which are incorporated herein by reference.

FIELD OF THE INVENTION

This invention generally relates to normal incidence ellipsometry, a non-destructive optical technique for measuring the properties of surfaces and thin films, and in particular to improvements to ellipsometric devices to extend the operating range of such devices.

BACKGROUND OF THE INVENTION

Ellipsometry is a sensitive optical technique for determining properties of surfaces and thin films. The shape and orientation of the reflected ellipse depend on the angle of incidence, the direction of polarization of the incident light, and the reflective properties of the surface being examined. The structural details of ellipsometers are more fully described in U.S. Pat. Nos. 6,449,043, 5,910,842 and 5,798,837, each of which is incorporated in this document by reference. Normal incidence ellipsometry is a widely used type of optical metrology, both for thin film measurements as well as scatterometry applications.

By including a rotating compensator that rotates about the propagating axis of the beam, certain limitations of rotating-polarizer or rotating-analyzer ellipsometers can be overcome. Such a configuration is commonly called a rotating compensator ellipsometer (RCE). The structural details of a prior art normal incidence rotating compensator ellipsometer are more fully described, e.g., in U.S. Pat. No. 7,173,700, which is incorporated herein by reference.

The prior art normal incidence rotating compensator ellipsometer describe in U.S. Pat. No. 7,173,700 includes an illumination source that produces a broadband probe beam. A polarizer is optically coupled to the probe beam to impart a known polarization state to the probe beam. The polarized probe beam is then optically coupled to a rotating compensator that is placed between the polarizer and a sample. The rotating compensator introduces a relative phase delay $\xi$ (phase retardation) between a pair of mutually orthogonally polarized components of the probe beam. The rotating compensator includes a rotating optical component, such as a waveplate, that delays the light polarized parallel to its slow axis relative to light polarized parallel to its fast axis by an amount proportional to the refractive index difference along the two directions and the thickness of the plate, and inversely proportional to the wavelength of the light. After leaving the compensator, the probe beam is directed at normal incidence against the surface of the sample. The sample reflects or scatters the probe beam back through the compensator and the polarizer, which acts as an analyzer for the beam returned from the sample. A detector measures the intensity of the returned probe beam as a function of rotational angle of the compensator or analyzer. A processor analyzes an output of the detector to obtain the quantities related to the complex reflectances $r_a$, $r_b$ of the sample. Such quantities include, e.g.: $|r_a|^2$, $|r_b|^2$, $\text{Re}(r_a r_b^*)$, and $\text{Im}(r_a r_b^*)$.

The complex reflectances $r_a$, $r_b$ refer to the reflectance coefficients of an anisotropic sample, such as a grating. By way of example, one reflectance (e.g., $r_a$) may be defined for light polarized parallel to the grooves of the grating. The other reflectance (e.g., $r_b$) may be defined for light polarized perpendicular to the grooves. The complex reflectances $r_a$, $r_b$ can also be used to define reflection coefficients of intrinsically anisotropic samples, in which case $r_a$ and $r_b$ correspond to reflectances for light polarized parallel to the two principal axes of the anisotropic material.

It is often advantageous to perform ellipsometry over a spectrum of wavelengths instead of a single wavelength source such as a laser Such a spectrum of wavelengths may be produced by a broadband light source, e.g. a Xenon and/or Oxygen arc lamp. All wavelengths are transmitted simultaneously through the system in a broadband probe beam and the different wavelength constituents returned from the sample may be separated in space after the polarizer by a dispersive element, such as a grating or a prism, and detected with an array detector such as a charge-coupled device (CCD) or a linear photo diode array (PDA). Such a broadband system, called a spectroscopic ellipsometer, offers the advantage of providing sample properties like the dielectric function of a material as a function of wavelength or, equivalently, energy. Further, spectroscopic ellipsometry is essential for samples with stratified single or multiple overlayers, which are encountered regularly in the manufacturing process of computer chips and memory devices. The penetration depth of light depends on the wavelength, so that the short wavelength part of the spectrum can be used to measure overlayer dielectric function as if it was bulk material, while the longer wavelengths penetrate deeper to reach the underlying interface, and together with knowledge of the dielectric function of the overlayer material provide the layer thickness. With thickness and dielectric function, the layer on top of the substrate may be comprehensively characterized.

Broadband operation is advantageous for many applications. Unfortunately, rotating compensator systems are not ideally suited for broadband operation. The difficulty encountered with RCE operation is a consequence of the fact that the retardation of the waveplate depends roughly inversely on the wavelength $\lambda$ of light. However, for best sensitivity, the retardation is preferably that of a quarter wave over the entire spectral range.

Current single rotating waveplate designs typically employ a waveplate that works reasonably well over a wide spectral range, yet, due to the dispersive nature of the material out of which the waveplate is constructed (e.g., $MgF_2$), the sensitivity is compromised at either the extremely short- or long wavelengths, or at both extremes. Specifically, with the retardation increasing towards the short wavelength end of the spectrum, the sensitivity of a rotating compensator ellipsometer gradually decreases and is reduced to that of an equivalent rotating polarizer system when it approaches 180°. Reducing the wavelength further, the sensitivity initially increases, assumes a second maximum at 270° but then hits a dead zone around 360° retardation, for which an RCE returns no phase information at all but becomes a simple off-axis reflectometer.

One could, in principle, circumvent wavelength restrictions of a conventional rotating-compensator system by constructing it with an achromatic compensator, such as a Fresnel rhomb. However, such achromatic compensator devices are non-trivial and expensive to manufacture, significantly bigger and heavier than standard waveplates, and generally feature unevenly distributed moments about the optical axis. Hence achromatic retarders are more difficult to use in a continuously, fast-rotating configuration than standard waveplates.

It is within this context that embodiments of the present invention arise.

BRIEF DESCRIPTION OF THE DRAWINGS

Objects and advantages of the invention will become apparent upon reading the following detailed description and upon reference to the accompanying drawings in which.

DESCRIPTION OF THE SPECIFIC EMBODIMENTS

Although the following detailed description contains many specific details for the purposes of illustration, anyone of ordinary skill in the art will appreciate that many variations and alterations to the following details are within the scope of the invention. Accordingly, the embodiments of the invention described below are set forth without any loss of generality to, and without imposing limitations upon, the claimed invention.

In embodiments of the present invention a second, different waveplate is introduced into a rotating compensator normal incidence ellipsometer. The second waveplate provides a quarter wavelength retardation that is different from and complementary to that of the first waveplate in order to increase the spectral range for which useful retardation is available, especially towards the deep UV portion of the electromagnetic spectrum. The sensitivity for the system may also be increased in the conventional spectral range, since each of the two waveplates may be optimized for its own, somewhat more narrow spectral range of operation. With the proper choice of two waveplates of different retardation, the useful spectral range can be extended from typically 190-820 nm to 150-1000 nm, and beyond if necessary, while increasing the sensitivity within the conventional wavelength range at the same time. To facilitate measurements operation in the deep UV range it may be useful to purge the optical path with an inert gas, e.g., nitrogen, to remove oxygen and other gases that tend to absorb UV radiation.

The ellipsometer may be operated with both waveplates rotating simultaneously and at a fixed ratio of rotation rates, or with one waveplate stopped. If the waveplate closest to the polarizer is stopped, its fast- (or slow-) axis may be aligned with the direction of the polarization light transmitted by the polarizer, in which case it turns into a neutral component.

If the system is set up to acquire data over the entire spectral range simultaneously, it is preferred to rotate both waveplates simultaneously, because it is the fastest way to obtain full spectral information.

The benefits of the proposed system include (1) an increase in diagnostic power due to extension of the spectral range into the very deep UV spectrum (at least 150 nm); (2) an overall increase in sensitivity for the conventional wavelength range; and (3) ease of construction which avoids expensive custom hardware and instead uses existing hardware for single rotating compensator ellipsometers, enabling the use of waveplates of high quality, custom retardation, and relatively low cost.

Figure 1:
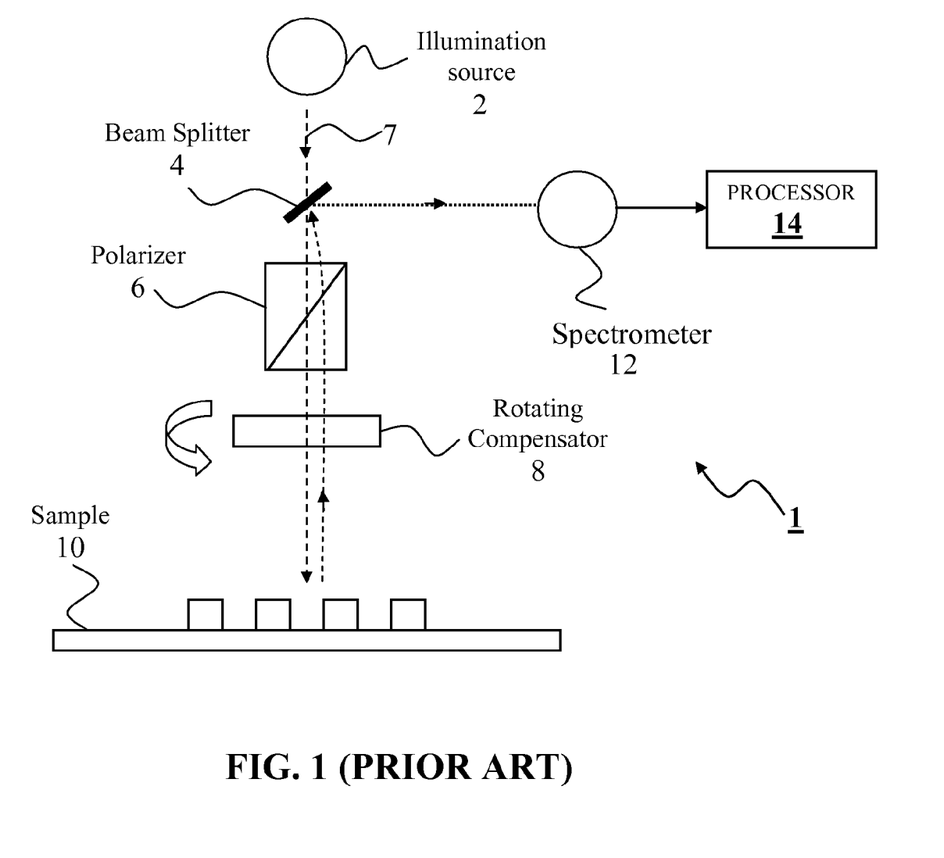
FIG. 1 is a schematic diagram of a prior art normal incidence rotating compensator ellipsometer.
Figure 2:
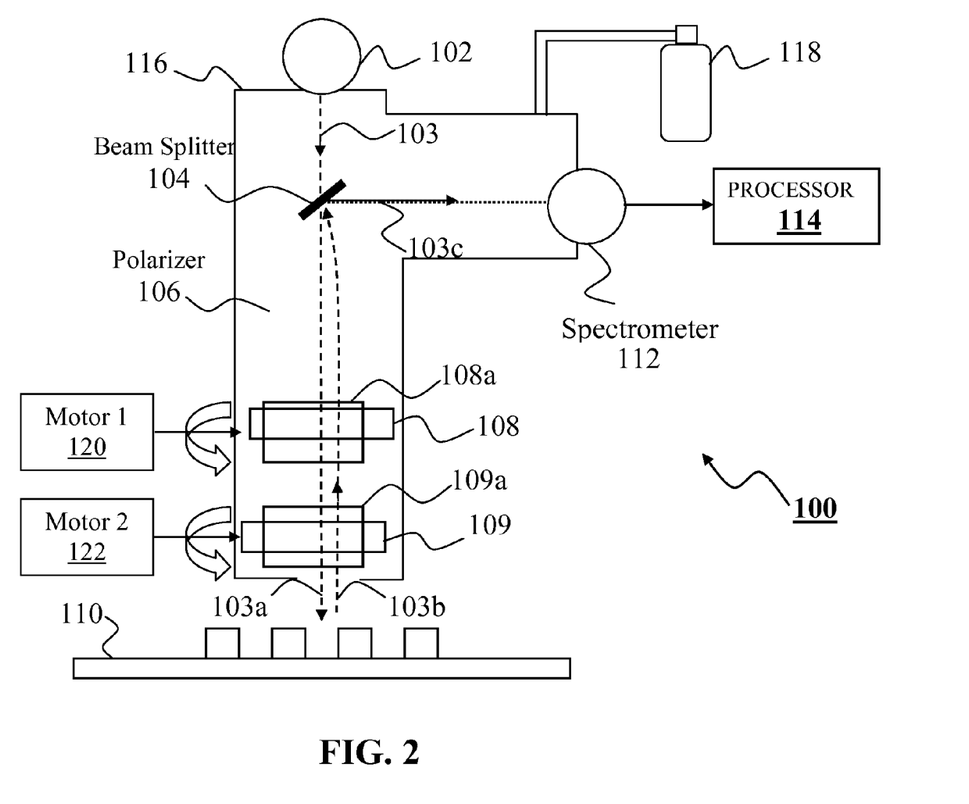
FIG. 2 is a schematic diagram of a normal incidence rotating compensator ellipsometer according to a first embodiment of the present invention.

Differences between the prior art and embodiments of the present invention may be understood by reference to FIG. 1 and FIG. 2.

The prior art apparatus is schematically illustrated in FIG. 1. A normal incidence ellipsometer 1 includes an illumination source 2. Illumination source 2 produces a broadband probe beam 7 that is projected through a beam splitter 4, polarizer 6 and rotating compensator 8 before reaching a sample 10. As it traverses this path, polarizer 6 imparts a known polarization state to the probe beam 7. Rotating compensator 8 introduces a relative phase delay $\xi$ (phase retardation) between a pair of mutually orthogonally polarized optical beam components of the probe beam 7. The amount of phase retardation is a function of the wavelength, the dispersion characteristics of the material used to form compensator 8, and the thickness of the compensator 8. Compensator 8 is rotated at an angular velocity $\omega$ about an axis substantially parallel to the propagation direction of the probe beam 7. Sample 10 returns the probe beam 7 (through polarizer 6 and rotating compensator 8) to beam splitter 4. Beam splitter 4 redirects the returning probe beam 7 to a spectrometer 12. Spectrometer 12 is typically a grating or prism combined with a charge coupled device (CCD) detector, but other technologies can also be used. The output of the spectrometer 12 is delivered to a processor 14 for analysis.

A normal incidence spectroscopic ellipsometer according to a first embodiment of the present invention is shown in FIG. 2. Normal incidence refers to light striking a surface at an angle perpendicular to the surface. A normal incidence broadband rotating compensator ellipsometer 100 includes a broad band light source 102. Light source 102 produces a broadband beam 103, which passes through beam splitter 104, polarizer 106 and first and second rotating compensators 108, 109 to produce a probe beam 103a. The probe beam 103a is directed to a sample 110, where it interacts with the sample (e.g., by reflection and/or scattering), thereby forming a sample beam 103b. The sample beam 103b is optically coupled back through the compensators 108,109 and the polarizer 106 to the beam splitter 104. A portion 103c of the sample beam 103b is optically coupled from the beam splitter to a spectrometer 112. An output of the spectrometer 112 is delivered to a processor 114 for analysis.

The broadband light source 102 produces the broadband beam 103 having a spectrum of polychromatic light over a predetermined wavelength range of interest. By way of example, for semiconductor materials and for thin films deposited on a substrate the range of interest may extend from 150 nm to 1000 nm. By way of example, the light source 102 may include a high pressure arc lamp (e.g., using Xenon and/or Oxygen) that produces a broadband probe beam 103 having wavelengths throughout the 150-1000 nm wavelength range of interest, however any comparable light source is sufficient for this application. Alternatively, the broadband light source 102 may produce a broadband beam 103 characterized by multiple discrete wavelengths that are distributed over a predetermined wavelength range of interest.

To facilitate operation at the lower end of the wavelength range, e.g., in the deep UV, the ellipsometer 100 may be configured to permit the beam path to be purged with an inert gas, such as nitrogen. Specifically, the optical components of the ellipsometer may be located within a housing 116 that is coupled to an inert gas source 118. Inert gas may flow from the source 118 to the housing 116 and through a space between the housing and the sample 110. This purges an optical path along which the broadband beam 103, probe beam 103a, sample beam 103b, and portion 103c pass.

Light source 102 is optically coupled to the beam splitter 104, which is optically coupled to the polarizer 106. Broadband probe beam 103 traverses an optical path from source 102, to beam splitter 104 and then to polarizer 106. Polarizer 106 imparts a known polarization state to the probe beam 103. A polarized beam 103a exits the polarizer to pass through the first rotating compensator 108 and the second rotating compensator 109 before striking the sample 110.

The first rotating compensator 108 is interposed along an optical path between the polarizer 106 and the second rotating compensator 109. The first rotating compensator 108 includes a quarter waveplate 108a mounted for rotation about an axis parallel to the light beam 103a, which is driven by a first motor 120. Rotating compensator 108 introduces a relative phase delay $\xi_1$ (phase retardation) between a pair of mutually orthogonally polarized optical beam components. The amount of phase retardation is a function of the wavelength, the dispersion characteristics of the material used to form the waveplate 108a of the first compensator 108, and the thickness of the wave plate 108a. In the first compensator 108 the waveplate 108a is rotated at an angular velocity $\omega_1$ about an axis substantially parallel to the propagation direction of the probe beam 103a. When used in this document, rotation is intended to include continuous rotation, as well as rotation in increments or steps.

The polarized beam 103a then passes through the second compensator 109. The second rotating compensator 109 comprises a second waveplate 109a mounted for rotation about an axis parallel to the light beam 103a, which is driven by a second motor 122. The second waveplate 109a introduces a relative phase delay $\xi_2$ (phase retardation) between a pair of mutually orthogonal polarized optical beam components to retard the signal of the polarized beam 103a incident to and reflected from the sample 110. The amount of phase retardation is a function of the wavelength, the dispersion characteristics of the material used to form the waveplate 109a, and the thickness of the waveplate 109a. The second waveplate 109a is rotated at an angular velocity $\omega_2$ about an axis substantially parallel to the propagation direction of beam 103a, by motor 122.

The quarter waveplate 109a of the second compensator 109 provides a quarter wavelength retardation which is different from and complementary to that of the first waveplate 108a of the first compensator 108 in order to increase the spectral range for which useful retardation is available, especially towards the deep UV spectrum. The sensitivity for the system may also be increased in the conventional spectral range, since each of the two waveplates 108a, 109a may be optimized for its own, somewhat narrower portion of the spectral range of operation.

Compensators 108 and 109 may be any conventional waveplate compensator. The thickness and material of the waveplates 108a,109a of the compensators 108, 109 are selected such that a desired range of phase retardations of the polarized beam 103a is induced over a range of wavelengths used to probe the sample 110. Preferably, the first compensator 108 and second compensator 109 are configured such that the waveplates 108a, 109a rotate synchronously. As used herein, the waveplates 108a, 109a may be said to rotate synchronously if an azimuth angle of the second plate 109a depends on an azimuth angle of the first waveplate 108a or vice versa. In particular, when the first waveplate 108a rotates at rotational speed $\omega_1$, the second waveplate 109a rotates with an angular speed $\omega_2$ that is proportional to $\omega_1$. In general, a proportionality factor relating $\omega_1$ and $\omega_2$ may be different from 1, i.e., $\omega_1$ and $\omega_2$ may be different from each other.

The sample beam 103b is directed from the sample 110 through polarizer 106 and rotating compensators 108,109 to the beam splitter 104. Beam splitter 104 redirects the portion 103c of the sample beam 103b to the spectrometer 112. By way of example, spectrometer 112 may include a grating or prism optically coupled to a photodetector, such as a charge-coupled device (CCD). Alternatively, other spectrometer and detector technologies can also be used. The output of the spectrometer 112 is delivered to the processor 114 for analysis. Data analysis for the system 100 is similar in principle to that performed for a conventional normal incidence rotating compensator ellipsometer with certain modifications to take into account additional Fourier components due to the multiple compensators. Such modifications may include synchronizing the rotation of the waveplates 108a, 109a and performing a somewhat more elaborate Fourier transform. However, these modifications may be implemented in software without otherwise impacting the hardware of the ellipsometer 100.

The ellipsometer 100 may be operated with both waveplates 108a, 109a rotating simultaneously and at a fixed ratio of rotation rates, or with one waveplate stopped. If waveplate 108a, which is closest to the polarizer 106 is stopped, its fast- (or slow-) axis may be aligned with the direction of polarization of the light transmitted by the polarizer 106, in which case it becomes a neutral component.

If the system is set up to acquire data over the entire spectral range simultaneously, it may be preferable to rotate both waveplates 108a, 109a simultaneously, because it is the fastest way to obtain full spectral information. The processor 114 may obtain intensity values from the spectrometer 112 at certain pre-defined and known waveplate (WP) azimuths. Using the known WP azimuth the processor 114 may carry out a discrete Fourier transform of the intensity values to extract polarization information from the measured intensity values.

The thickness and material of the second waveplate 109a may be selected such that a desired range of phase retardations of the beam 103a is induced by the range of wavelengths used to probe the sample 110. In the ideal case of truly complementary waveplates, the information returned provides much extended spectral sensitivity, by means of operation in an ideal band of retardation.

A preferred thickness ratio of the two waveplates 108a, 109a for the complementary dual compensator configuration, may be determined by the range of ideal retardation. By way of example, 90° of retardation may be regarded as ideal, and a range of 45° to)135° (90°+/−45° may be considered acceptable. The sensitivity of one of the Fourier coefficients varies as the sine of the retardation: at 45° or 135° the sensitivity is reduced to 1/√2, about 70% of the maximum value. Conversely, the range of useful retardation may be wider if the system is allowed to operate at lower sensitivity.

For the example set forth above (90°+/−45° retardation), the ideal ratio of waveplate thicknesses is ⅓. In particular, the ratio of thickness is independent of (1) material dispersion and (2) wavelength range of operation. As it turns out, the ideal thickness ratio is determined by an entirely general relationship. While the thickness ratio of the waveplates is general, picking the thickness of the first waveplate 110a is not arbitrary: the two relevant parameters are the spectral range of the system and the properties of the material out of which the waveplate 110a is to be constructed. Therefore, spectral range of the ellipsometer application, optical properties of the compensator, and the acceptable deviation from 90 degree retardation (band of operation) determines (1) the absolute thickness of the waveplates and (2) the number of waveplates that are needed to stay within the acceptable band of retardation over the available spectral range. To obtain useful data at the lower end of the spectral range, it is necessary to use a thinner waveplate.

Figure 3:
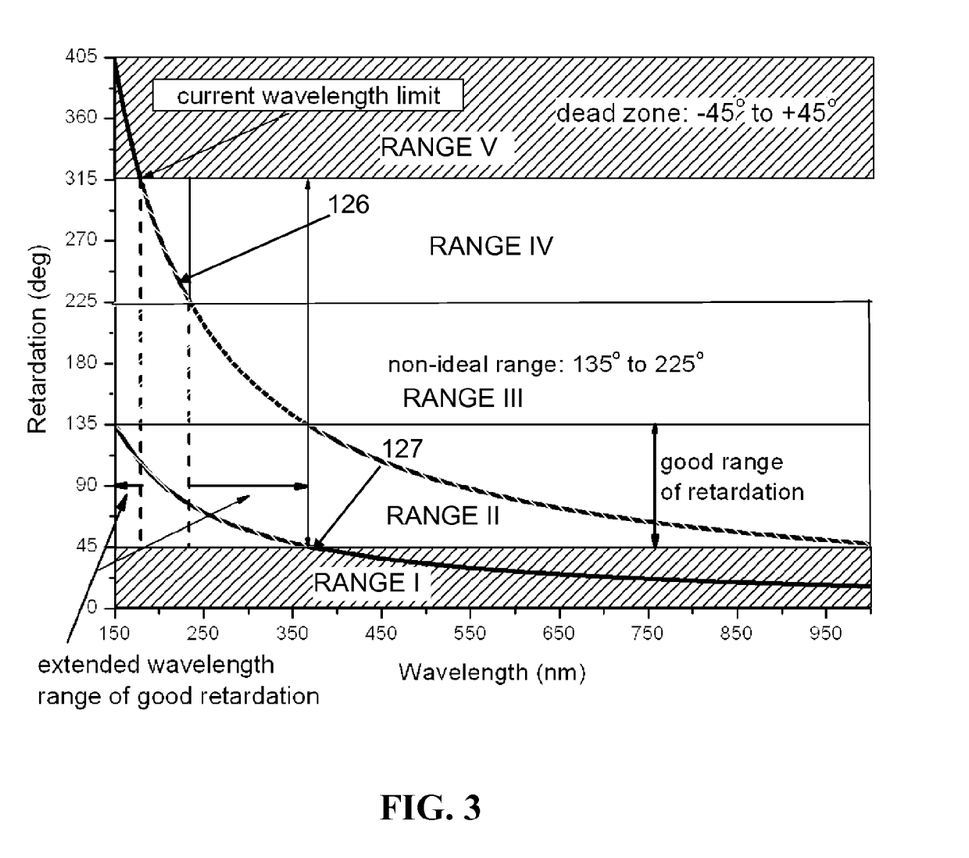
FIG. 3 is a graph illustrating retardation curves for two different waveplates from 150 nm to 1000 nm.

Advantages of a dual rotating compensator ellipsometer of the type shown in FIG. 2 may be understood by referring to FIG. 3, which is a graphical representation of retardation (degrees) versus wavelength (nm) for two different waveplates from 150 nm to 1000 nm. The graph shown in FIG. 3 is broken up into five regions from 0 degrees to 415 degrees: Range I from 0° to 45°, Range II from 45° to 135°, Range III from 135° to 225°, Range IV from 225° to 315°, and Range V from 315° to 415° (essentially a dead zone from −45° to +45°), and shows the retardation curves for two different $MgF_2$-waveplates. Ideally, it is preferred to operate at a 90° phase-shift throughout the entire spectral range. However, this is usually not possible due to the wavelength dependence of the relative phase-shift in the birefringent materials of the waveplates. The upper curve 126 represents the retardation of a standard waveplate 108a. In this example the retardation is within Range II, an acceptable range for wavelengths from 370 to 1000 nm. However, use of such a waveplate all the way to 190 nm, traversing the range of retardations in Range II, from 135° to 225°, i.e., around 180°, is not an ideal range of operation; in Range IV, close to 300 nm the 180° crossing occurs, for which the signal from the waveplate 108a returns information that is equivalent to that from the less desirable rotating compensator system depicted in FIG. 1. Further, below 300 nm the retardation of the waveplate 108a rapidly increases towards the short wavelength extreme of the available spectral range and reaches 360° at 160 nm. A dead-zone of significantly reduced sensitivity, designated in FIG. 3 as Range V, starts at about 180 nm. At 360° the first waveplate 108a returns no phase information about the sample whatsoever, but behaves as a simple off-axis reflectometer.

A lower curve 127 represents the retardation of the thin waveplate 109a of the second compensator 109 of the ellipsometer 100 and fills in at the short wavelength end. The retardation of the second waveplate 109a only reaches 135° at 150 nm and hence stays within a desirable range (Range II) of retardation angles from 150 nm to roughly 370 nm. Above about 370 nm, the standard waveplate 108a enters its optimal spectral range coming down from 135° and takes over. The ideal range of operation may therefore be extended by more than 200 nm from 360 nm all the way to 150 nm in this example through the use of two complementary rotating waveplates 108a, 109a. Of particular importance is the fact that the dead-zone from 150 to 180 nm in which a prior art system cannot operate may be completely avoided through use of a second waveplate.

From the foregoing it may be seen that spectroscopic ellipsometers according to embodiments of the present invention may utilize different waveplates selected to provide phase retardations within an effective range of retardations (e.g., range II or a combination of range II and range III) for complementary wavelength ranges. As used herein, the wavelength ranges for which the waveplates produce retardations in the effective range are said to be complementary if the corresponding wavelength ranges are at least partly non-overlapping.

Figure 4:
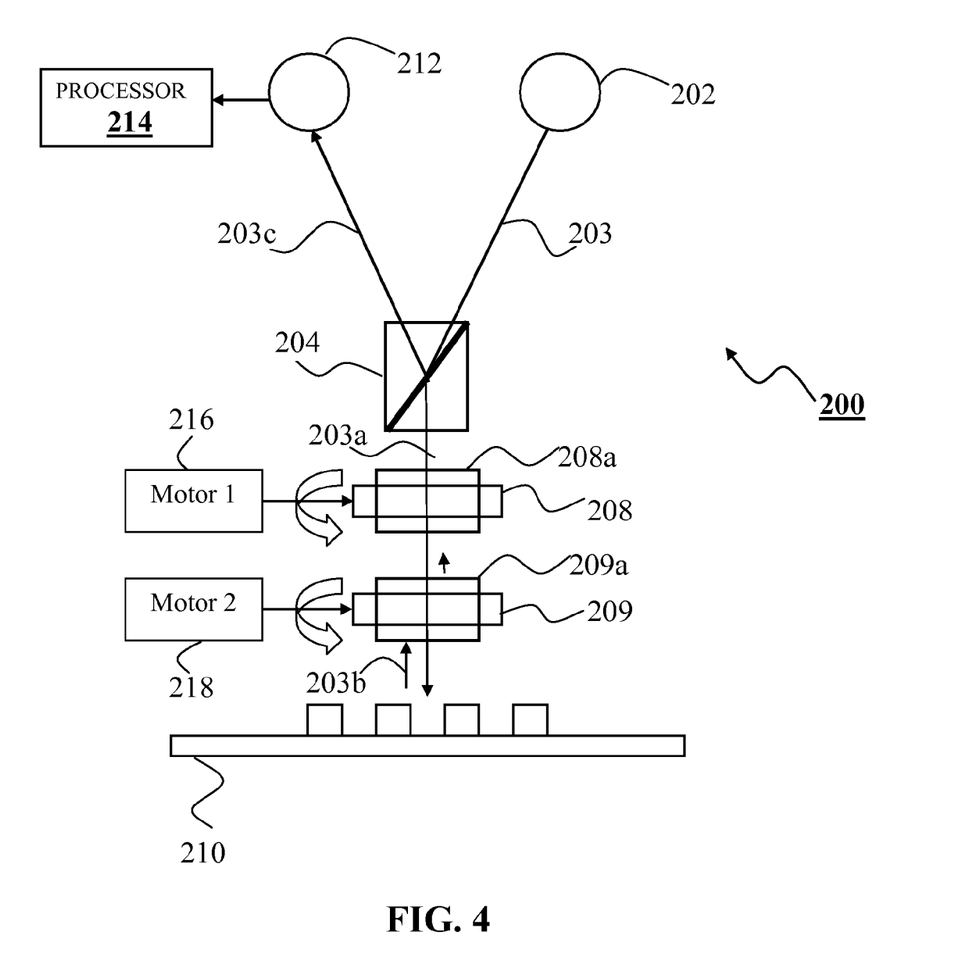
FIG. 4 is a schematic diagram of a normal incidence rotating compensator ellipsometer according to a first alternate embodiment of the present invention.

FIG. 4 schematically illustrates a normal incidence ellipsometer 200 according to a first alternate embodiment of the present invention. Ellipsometer 200 shares many of the components described for ellipsometer 100 with the main difference being that the beam splitter 104 and polarizer 106 have been replaced by a beam splitting polarizer 204. Beam splitting polarizer 204 may be a Wollaston prism or equivalent and performs two functions. The first is to function as a beam splitter/combiner. The second is to impart a known polarization state to radiation 203. Polarizer 204 imparts a known polarization state to the probe beam 203. A polarized beam 203a exits the polarizer to pass through a first rotating compensator 208, which is driven by a first motor 216, and a second rotating compensator 209, which is driven by a first motor 218, before striking a sample 210. As the probe beam 203a is scattered by the sample 210, beam splitting polarizer 204 directs a portion 203c of the scattered probe beam 203b to spectrometer 212. The output of the spectrometer 212 is delivered to a processor 214 for analysis.

Figure 5:
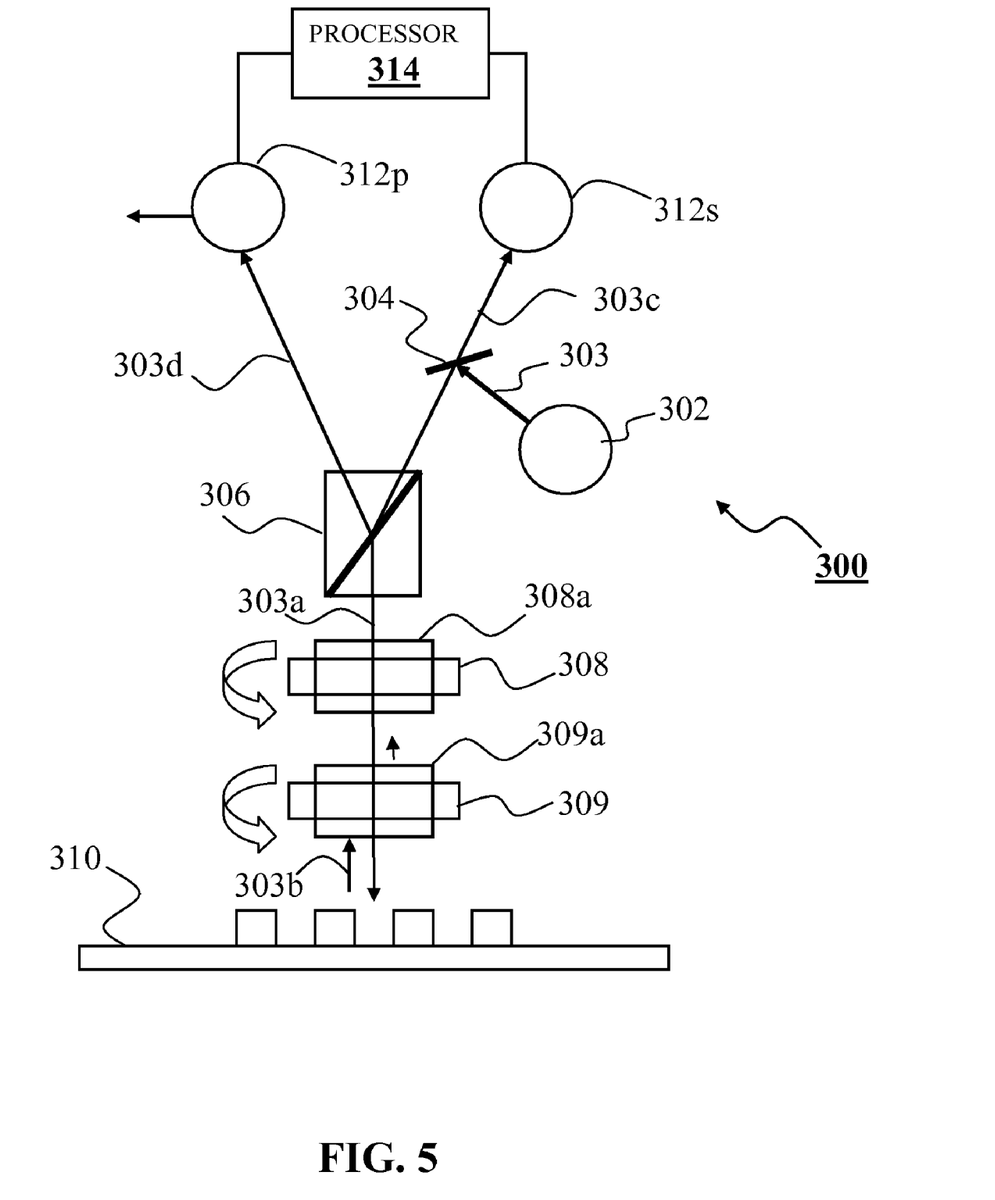
FIG. 5 is a schematic diagram of a normal incidence rotating compensator ellipsometer according to a second alternate embodiment of the present invention.

As shown in FIG. 5, a second alternate embodiment comprises a normal incidence ellipsometer 300 which includes a broad band light source 302. Broad band light source 302 produces a broadband probe beam 303 that is optically coupled to a beam splitter 304 and a beam splitting polarizer 306. As it traverses this path, polarizer 306 imparts a known polarization state to the probe beam 303. The polarized beam 303a is optically coupled to first rotating compensator 308 and second rotating compensator 309 before reaching a sample 310. Rotating compensators 308, 309 introduce a relative phase delay ξ between a pair of mutually orthogonally polarized optical beam components. The amount of phase retardation is a function of the wavelength, the dispersion characteristics of the material used to form compensators 308,309 and the thickness ratio for the quarter waveplates 308a, 309a of the compensators 308, 309. The ellipsometer 300 may be operated with both waveplates 308a, 309a rotating simultaneously and at a fixed ratio of rotation rates, or with one waveplate stopped. Compensators 308,309 are rotated about an axis substantially parallel to the propagation direction of the probe beam. If waveplate 308a, which is closest to the polarizer 306 is stopped, its fast- (or slow-) axis may be aligned with the direction of polarization of the light transmitted by the polarizer 306, in which case it turns into a neutral component. Sample 310 returns the probe beam 303 (through polarizer 306 and rotating compensators 308, 309) to beam splitter 304.

Beam splitting polarizer 306 may be a Wollaston prism or equivalent which imparts a known polarization state to the probe beam 303 and functions as a beam splitter/combiner. As a return probe beam 303b returns from sample 310, beam splitting polarizer 306 splits the returning probe beam 303b into two components 303c, 303d. The first component 303c (referred to as s-polarized) is characterized by having detected polarization identical with that of the illuminating polarization, and is directed to s-spectrometer 312s. The orthogonally polarized return component 303d is designated p-polarized, and is directed to p-spectrometer 312p. Spectrometer 312s and 312p are typically monochrometer-CCD detector combinations, but other technologies can also be used. The spectrometers 312s, 312p deliver signals to a processor 314 for analysis.

Although embodiments of the invention are shown and described as involving two complementary rotating waveplate compensators, the concept may be extended to ellipsometry involving three or more complementary rotating waveplate compensators. Phase retardations of the polarization state of a probe beam may be introduced over additional ranges of wavelengths with additional compensators. Each additional range of wavelengths and each additional compensator can be selected such that additional phase retardation values induced over a corresponding additional range of wavelengths lies within a range of effective phase retardations. Each additional compensator can be configured to induce effective phase retardation values within a primary range of effective retardations that is outside of a complementary to the effective phase retardation values induced by the other compensators apparatus.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. In the claims that follow, the indefinite article "A", or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. A normal incidence ellipsometer apparatus comprising:
   a light source configured to generate a polychromatic light beam characterized by a range of optical wavelengths;
   a polarizer optically coupled to the illumination source and configured to impart a known polarization state to the light beam before the light beam interacts with a sample;
   a first compensator disposed in the path of the light beam configured to induce phase retardations of a polarization state of the light beam, wherein the first compensator is configured such that at least a first effective phase retardation value is induced over a first range of wavelengths by the first compensator, wherein a first effective phase retardation value is within a range of effective retardations;
   a second compensator disposed in the path of the light beam configured to induce phase retardations in a polarization state of the light beam before the probe beam is incident on the sample along an optical path normal to the sample, wherein the second compensator is configured such that at least a second effective phase retardation value is induced over a second range of wavelengths by the second compensator, wherein the second range of wavelengths is complementary to the first range of wavelengths, and wherein the second effective phase retardation value is within the range of effective retardations;
   each of said first and second compensators being rotatable about an axis substantially parallel to the propagation direction of the light beam; and
   a detector configured to interact with a portion of the light beam that interacts with the sample and with said first and second compensators, wherein the detector is configured to measure an intensity of light as a function of wavelength and of a rotation angle of each of the first and second compensators about its respective axis.

2. The apparatus as recited in claim 1 that further comprises: a beam splitter for dividing the probe beam after its interaction with the sample into two components, the first component having polarization that is identical to the known polarization state, and the second component having polarization that is orthogonal to the known polarization state.

3. The apparatus of claim 1, further comprising:
   a processor optically coupled to the detector and configured to determine a polarization state of the light after interaction of the probe beam with the sample, from the intensities measured by the detector.

4. The apparatus of claim 1, wherein the polarizer and the compensators are configured such that at least a portion of the probe beam incident on the sample is scattered from the sample and passes back through the compensators and the polarizer and is optically coupled to the detector.

5. The apparatus of claim 1, wherein the first compensator and the second compensator each comprise a quarter waveplate, and the first and second compensators rotate at the same time but not at the same speed.

6. The apparatus of claim 5, wherein rotation speeds of the first and second compensators are configured to rotate synchronously.

7. The apparatus of claim 1, wherein the first compensator and the second compensator each comprise a quarter waveplate, and one waveplate is parked in a neutral position in the probe beam, while the other one is spinning.

8. The apparatus of claim 1, wherein the first and second compensators are selected such that an optical wavelength range of the apparatus is between 150 nm to 1000 nm.

9. The apparatus of claim 1, further comprising means for purging an optical path of the light beam through the apparatus with an inert gas.

10. An apparatus configured to direct an illumination source against a sample at a normal angle of incidence to evaluate the sample, the apparatus comprising:
    an illumination source configured to generate a probe beam of polychromatic light having a range of optical wavelengths for interacting with the sample;
    a polarizer optically coupled to the illumination source and configured to impart a known polarization state to the probe beam before the probe beam interacts with the sample;
    a first rotating compensator optically coupled to the polarizer and configured to induce a first phase retardation value in the polarization state of the probe beam over a first range of wavelengths;
    a second rotating compensator optically coupled to the first rotating compensator and configured to induce a second phase retardation value in the polarization state of the probe beam before the probe beam interacts with the sample over a second range of wavelengths, wherein the second range of wavelengths is complementary to the first range of wavelengths;
    the phase retardations in the polarization state of the probe beam induced by both first and second compensators before the probe beam reaches the sample and after it has been reflected by the sample;
    said first and second compensators being configured such that at least the first effective phase retardation value induced by the first compensator is within a primary range of effective retardations, and the second effective phase retardation value induced by the second compensator is outside of and complementary to said primary range;

the polarizer configured to interact with the probe beam after the reflected probe beam has returned through the compensators; and a detector configured to measure the intensity of the probe beam after interaction with the sample as a function of the rotational angles of the compensators.

11. The apparatus as recited in claim 10 that further comprises:

a beam splitter configured to divide the probe beam after its interaction with the sample into two components, the first component having polarization that is identical to the known polarization state, and the second component having polarization that is orthogonal to the known polarization state.

12. The apparatus as recited in claim 11 wherein the polarizer is further configured to act as a beam splitter to divide the probe beam after its interaction with the sample into two components, the first component having polarization that is identical to the known polarization state, and the second component having polarization that is orthogonal to the known polarization state.

13. The apparatus of claim 10, further comprising:

a processor coupled to the detector and configured to determine the polarization state of the light after interaction of the probe beam with the sample, from the intensities measured by the detector.

14. The apparatus of claim 10, wherein the first compensator and the second compensator each comprise a quarter waveplate, and the first and second compensators rotate at the same time but not at the same speed.

15. The apparatus of claim 14, wherein the first and second compensators are configured to rotate synchronously.

16. The apparatus of claim 10, wherein the first compensator and the second compensator each comprise a quarter waveplate, and one waveplate is parked in a neutral position in the probe beam, while the other one is spinning to define a pseudo-single-compensator mode for the apparatus.

17. The apparatus of claim 10, wherein first and second waveplates are configured such that a combination of the first and second wavelength ranges includes a wavelength range from 150 nm to 1000 nm.

18. The apparatus of claim 10 wherein the range of effective retardations includes phase retardations between 45° and 135°.

19. The apparatus of claim 10 wherein the range of effective retardations includes phase retardations of between 225° and 315°.

20. An ellipsometry method for evaluating a sample comprising:

a) generating a beam of polychromatic light characterized by a range of wavelengths or a plurality of discrete wavelengths;

b) polarizing the light to impart a known polarization state to the light beam;

c) inducing phase retardations of the polarization state of the light beam over a first range of wavelengths with a first compensator, wherein the first range of wavelengths and the first compensator are selected such that at least a first effective phase retardation value induced over the first range of wavelengths lies within a range of effective phase retardations;

d) inducing phase retardations of the polarization state of the light beam over a second range of wavelengths with a second compensator before at least a portion of the light beam interacts with the sample at normal incidence, wherein the second range of wavelengths is complementary to the first range of wavelengths, wherein the second range of wavelengths and the second compensator are selected such that at least a second effective phase retardation value induced over the second range of wavelengths range lies within the range of effective phase retardations;

e) said first and second compensators being configured such that at least the first effective phase retardation value induced by the first compensator is within a primary range of effective retardations, and the second effective phase retardation value induced by the second compensator is outside of and complementary to said primary range; and f) measuring an intensity of the light beam after interaction of the light beam with the sample.

21. The method as recited in claim 20 that further includes the step of:

dividing the probe beam after its interaction with the sample into two orthogonally polarized components.

22. The method of claim 21, further comprising coupling each of the orthogonally polarized components to a different detector.

23. The method of claim 22 that further includes the step of:

determining the polarization state of the light after interaction of the probe beam with the sample with a processor operably coupled to the detector, from the intensities measured by the detector.

24. The method of claim 20 that further includes the step of:

rotating the first and second compensators at the same time but not at the same speed, in order to keep the information associated with each waveplate separate, wherein the first compensator and the second compensator each comprise a quarter waveplate.

25. The method of claim 24 wherein the first and second compensators rotate synchronously.

26. The method of claim 20 that further includes the step of:

parking one compensator in a neutral position in the probe beam, while the other one is spinning, wherein the first compensator and the second compensator each comprise a quarter waveplate.

27. The method of claim 20, wherein the range of optical wavelengths is 150 nm to 1000 nm.

28. The method of claim 20, further comprising purging an optical path of the light beam with an inert gas.

29. The method of claim 20, further comprising inducing phase retardations of the polarization state of the light beam over one or more additional ranges of wavelengths with one or more additional compensators, wherein each additional range of wavelengths and each additional compensator are selected such that one or more additional phase retardation values induced over the corresponding additional range of wavelengths lies within a range of effective phase retardations, wherein each additional compensator is configured such that at least the one or more effective phase retardation values induced by the additional compensator is within a primary range of effective retardations, and the effective phase retardation values induced by the first and second compensators and other additional compensators is outside of and complementary to said primary range.

* * * * *